United States Patent [19]

Ham

[11] Patent Number: 4,540,750
[45] Date of Patent: Sep. 10, 1985

[54] DIETHYL TOLUENE DIAMINE HARDENER SYSTEMS

[75] Inventor: Nancy M. Ham, Williamston, Mich.

[73] Assignee: Ciba-Geigy Corporation, Ardsley, N.Y.

[21] Appl. No.: 653,417

[22] Filed: Sep. 24, 1984

[51] Int. Cl.$^3$ .............................................. C08G 59/64
[52] U.S. Cl. ..................................... 525/504; 525/523; 525/526; 528/99; 528/111; 528/361; 528/407
[58] Field of Search ....................... 525/504, 523, 526; 528/99, 111, 407, 361

[56] References Cited

U.S. PATENT DOCUMENTS 4,447,586 5/1984 Shimp ............................ 528/407 X

OTHER PUBLICATIONS

Andres et al., "Hardenable Epoxy Molding Compositions", Chem. Abstr., 76, 128157t, (1972).
Urech et al., Chem. Abstr., 96, 218822y, (1982).

Primary Examiner—Earl Nielsen
Attorney, Agent, or Firm—Harry Falber

[57] ABSTRACT

A resinous hardener system comprising the reaction product of diethyl toluene diamine and an epoxide having a functionality of at least two, the hardener being capable of incorporation into a variety of epoxy and urethane resins.

19 Claims, No Drawings

DIETHYL TOLUENE DIAMINE HARDENER SYSTEMS

Adducts from amines and mono- and diepoxides have long been used in industry as curing agents for epoxy resins. The advantages of the formation of such adducts include lower volatility, lower irritation potential, reduced tendency to blush and exude, and the like. Such adducts and the advantages thereof are discussed in Lee and Neville, Handbook of Epoxy Resins, McGraw Hill (1967). It is to be noted, however, that such adducts may not exhibit significant improvement in chemical resistance over that of their free amine counterparts.

More specifically, such adducts have been prepared from diethylenetriamine with diglycidylethers of bisphenol A of varying molecular weight. These epoxy resins have all exhibited a functionality of not more than two and have exhibited various improved performance characteristics. As previously noted, however, they have been deficient in the important characteristic of resistance to chemical attack, and primarily to solvent attack.

Likewise, methylene dianiline-digylcidyl ether bisphenol A is a preferred curing agent for heat resistant epoxy resin compounds. However, methylene dianiline is considered a carcinogen by the Environmental Protection Agency.

For example, U.S. Pat. Nos. 3,655,624, 3,704,281 and 3,996,186 disclose adducts of triglycidyl isocyanurate and amines. These adducts are solid in form, are noted for use in molding materials and are generally inferior in terms of solvent resistance. Thus, these materials would have limited value as protective coatings.

Additionally, U.S. Pat. Nos. 3,538,184, 3,625,918 and 3,629,181 disclose amine adducts which are based on epoxy resins of the bisphenol A type or are alicyclic epoxy resins. While such adducts exhibit improved handling and mechanical properties, it is to be noted that the resins used therein have a functionality of not more than two and that the adducts are again deficient in the important characteristic of resistance to chemical attack.

Other corresponding systems are disclosed in U.S. Pat. Nos. 3,996,175 and 4,348,505.

It is the primary object of this invention to prepare novel liquid adducts of diethyl toluene diamine and di- and polyepoxides.

It is a further object to provide adducts for use as curing agents for epoxy and urethane resins.

It is still a further object to provide such curing agents which overcome the disadvantages of prior art curing agents when said curing agents are combined with a wide variety of epoxy and urethane resins.

Further objects and advantages of this invention will become apparent from the following descriptive material and illustrative examples.

It has now been surprisingly discovered that the preparation of diethyl toluene diamine adduct curing agents with epoxides of functionality of at least two or urethanes enhances the performance characteristics of the cured epoxy and urethane products. Relative to epoxy resins, in contrast to the free amine counterpart which requires an excessively long time to cure to a B-stage at room temperature because of its limited reactivity with epoxy resins, the instant adduct substantially shortens the cure time without a significant reduction in physical properties. Formulated hardeners can be prepared from these adducts to cure at room temperature or to cure to a "B stage" at room temperature and reflow at elevated temperatures. Hardeners formulated from these adducts are especially useful in making heat cured laminates where a reflow system aids in obtaining optimum properties. The reflow hardeners of this invention will cure to a semi-solid B stage at room temperature and then return to a liquid at an elevated temperature. When used in a laminate, a reflow system allows the resin to thoroughly penetrate the fibers and avoid air pockets. The absence of air pockets allows the laminate to be used at higher temperatures with increased stability. Additionally, such adducts are not viewed as carcinogens, are non-staining and are liquid at room temperature.

Diethyl toluene diamine corresponding to the formula

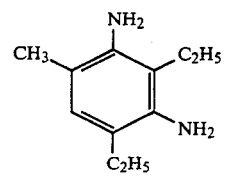

is the dominant diamine component. It is to be noted, however, that other positional isomers such as 2-methyl-4, 6-diethyl-1,3-benzene diamine may be present in combination with the above noted isomer as the applicable diamine component for purposes of this invention. Commercially available diamines will generally comprise about 75% of the 2,4-diethyl isomer and about 20% of 4,6-diethyl isomer with the remainder consisting of other related components.

The multifunctional epoxide component can be selected from a broad range of aliphatic and aromatic epoxies having a functionality of at least two. Typical materials include diglycidyl ether of bisphenol A, epoxy phenol novolacs, 1,4-butane diol diglydicyl ether, epoxy cresol novolacs, triglycidyl para-amino phenol, triglycidyl tris(p-hydroxyphenyl)methane, tetraglycidyl-1,1,2,2 tetrakis (p-hydroxyphenyl)ethane, vinyl cyclohexene dioxide, N,N,N¹,N¹-tetraglycidyl-4,4¹ methylene bis-benzeneamine, N,N,N¹,N¹-tetraglycidyl meta-xylene diamine, diglycidyl aniline, resorcinol diglycidyl ether, the diglycidyl ethers of catechol, hydroquinone, and the like, diglycidyl ortho-toluidine, diglycidyl isophthalate, bisphenol F and S epoxy resins, and N,N,N¹,N¹-tetraglycidyl 1,3 bis-amino-methylcyclohexane. The various ethers may be substituted on the respective phenyl rings by such non-reactive substituents as alkyl, halogen, and the like.

Preferred components correspond to
(a)

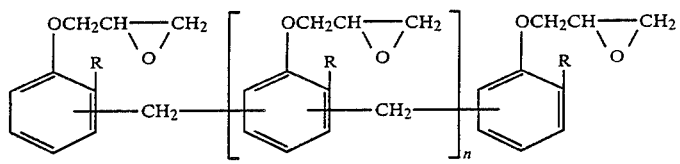

wherein R is hydrogen or methyl, and n is 0.2–3.4. These components are exemplified by the epoxidation products of cresol novolacs and phenol novolacs of varying molecular weight. The preparation of such materials is well known in the art.

(b) diglycidyl ethers of bisphenols corresponding to the formula

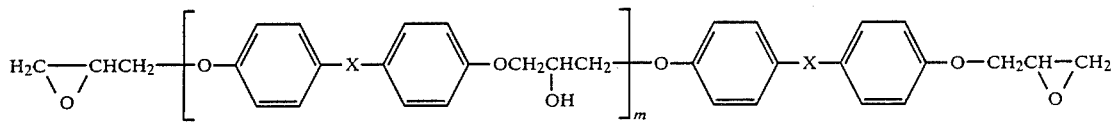

wherein m is 0–50 and X is —CH$_2$—,

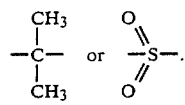

These represent, respectively, bisphenols F, A and S.

(c) 1,4-butanediol diglycidyl ether.

The new adducts of this invention are generally prepared by charging the amine to the reaction vessel and heating to a temperature of 80° to 100° C. The polyepoxide, preferably preheated, is then added over a period of from 60 to 180 minutes, allowing a maximum exotherm up to about 125° C. At the conclusion of the polyepoxide feed, the reaction mixture is generally heated to 80° 1 to 125° C. for a period of about 2 to 6 hours, to ensure completeness of the reaction. The progress of the reaction can be followed by titration of the epoxide groups using samples taken during the reaction, completion being indicated by the absence of epoxy groups. The adducts are liquid at room temperature with medium viscosity.

With regard to the relative concentrations of the components, the diamine is present in excess in the preparation of the adducts. Thus, mole ratios of from about 2 to 10 moles of diamine per mole of epoxy are utilized with 4 to 8 moles of diamine per mole of epoxy being preferred and 6 moles of diamine per mole of epoxy being particularly preferred.

Other amines may be optionally added to the adducts in order to provide hardeners which yield specifically desired properties in the cured resins.

As suitable amines, there may be mentioned aliphatic, cycloaliphatic or aromatic primary and secondary amines, with the aliphatic and cycloaliphatic amines being preferred. Typical amines include monoethanolamine, N-aminoethyl ethanolamine, ethylenediamine, hexamethylenediamine, trimethylhexamethylenediamine, diethylenetriamine, triethylenetetramine, tetraethylenepentamine, N,N-dimethylpropylenediamine-1,3, N,N-diethylpropylenediamine-1,3, bis(4-amino-3-methylcyclohexyl)methane, bis(p-aminocyclohexyl)methane, 2,2-bis(4-aminocyclohexyl)propane, 3,5,5-trimethyl-s-(aminomethyl)-cyclohexylamine, N-aminoethyl-piperazine, m-phenylene-diamine, p-phenylenediamine, bis(p-aminophenyl)methane, bis(p-aminophenyl)-sulfone, m-xylylenediamine, toluene diamine, 1,2-diaminocyclohexane, 1,4-diaminocyclohexane, 1,3-bis(aminomethyl)cyclohexane, 1,4-bis(aminomethyl)cyclohexane, isophorone diamine and 1-methyl-imidazole. Preferred amines include diethylenetriamine, triethylenetetramine, tetraethylenepentamine, 1,2-diaminocyclohexane, bis(p-aminocyclohexyl)methane, m-xylylenediamine, isophorone diamine, 1,4-bis(aminomethyl)cyclohexane, N-aminoethyl-piperazine, 1,3-bis(aminomethyl)cyclohexane, bis(p-aminophenyl)methane and 1-methyl imidazole.

These amines are present in maximum concentrations of about 75%, by weight of the total composition, and preferably in a maximum concentration of 55%, by weight.

As previously noted, the modified hardener systems can be processed with a wide variety of epoxy resins. Included among such resins are epoxide resins based on polyhydric phenols such as those based on bisphenol A, F, and S, epoxidation products of cresol novolacs, and epoxidation products of phenol novolacs; hydantoin epoxide resins; polyglycidyl esters; glycidylated aromatic amines; glycidylated aminophenols; and certain cycloaliphatic epoxy resins. In adhesive, coating and filament winding applications, resin based on the diglycidyl ether of bisphenol A is widely used. The modified hardener is utilized in stoichiometric amounts ±50% relative to the epoxy resin, with 85% of stoichiometry being preferred.

Apart from the above areas of utility, the aducts of this invention are useful as curing agents for a wide variety of epoxy resins in various heat cured applications. When combined with di- and polyepoxides, at generally stoichiometric amounts, and cured at elevated temperatures, a network of high crosslink density occurs. Accordingly, the expression "cure" as used herein, denotes the conversion of the above adducts and epoxide material into insoluble and infusible crosslinked products, with simultaneous shaping to give shaped articles such as castings, pressings or laminates, or to give two-dimensional structures such as coatings, enamels or adhesive bonds. The modified hardener system is particularly advantageous for the formation of coatings because of the improved compatibility with resins and the improved toughness of the resulting cured coatings.

The adducts prepared according to the invention and admixed with other polyepoxide compounds can furthermore be mixed, at any stage before cure, with usual modifiers such as extenders, fillers and reinforcing agents, pigments, dyestuffs, organic solvents, plasticizers, tackifiers, rubbers, accelerators, diluents, and the like. As extenders, reinforcing agents, fillers and pigments which can be employed in the curable mixtures according to the invention there may be mentioned, for example: coal tar, bitumen, glass fibers, boron fibers, carbon fibers, cellulose, polyethylene powder, polypropylene powder, mica, asbestos, quartz powder, gypsum, antimony trioxide, bentones, talc, silica aerogel ("Aerosil"), lithopone, barite, calcium carbonate, titanium dioxide, carbon black, graphite, iron oxide, or metal powders such as aluminum powder or iron powder. It is also possible to add other usual additives, for example, flameproofing agents, agents for conferring thixotropy, flow control agents such as silicones, cellulose acetate butyrate, polyvinyl butyral, waxes, stearates and the like (which are in part also used as mold release agents) to the curable mixtures.

The accelerators, when utilized, function to speed the curing operation in the preparation of thin films, i.e. films of a maximum of 8 mil thickness per coat. Typical accelerators include aromatic acids such as benzoic and salicylic acids; phenols such as phenol, p-tert.butyl phenol, bisphenol A and nonyl phenol; and aromatic alcohols such as benzyl alcohol.

The solvents modify the curable blends, particularly serving to control viscosity. Applicable solvents include ether alochols such as ethylene glycol monomethylether, mono-ethylether, monobutylether, and the diethylene glycol analogs; aromatic hydrocarbons such as xylene and toluene; and the like.

It is also possible in adhesive formulations, for example, to add rubbers such as carbonyl-terminated acrylonitrile-butadiene rubber, modifying resins such as triglycidyl p-aminophenol, accelerators such as boron trifluoride monoethylamine complexes or imidazole complexes, and other additional hardeners such as dicyandiamide.

The curable mixtures can be manufactured in the usual manner with the aid of known mixing equipment (stirrers, kneaders, rollers and the like).

The curable epoxide resin mixtures are especially useful in the fields of surface protection, the electrical industry, laminating processes and the building industry. They can be used in a formulation which is in each case suited to the particular end use, in the unfilled or filled state, optionally in the form of solutions or emulsions, as paints enamels, sintering powders, compression molding compositions, dipping resins, casting resins, injection molding formulations, impregnating resins and adhesives, as tooling resins, laminating resins, sealing and filling compositions, floor covering compositions and binders for mineral aggregates. Of primary interest, is their utility in making heat cured laminates wherein the previously noted reflow properties aid in obtaining optimum performance characteristics. Thus, the formulated hardeners are especially useful in making heat cured laminates where a reflow system aids in obtaining optimum properties. As previously noted, the reflow hardeners of this invention will cure to a semi-solid B state at room temperature and then return to a liquid at an elevated temperature. When used in a laminate, a reflow system allows the resin to thoroughly penetrate the fibers and avoid air pockets. The absence of air pockets allows the laminate to be used at higher temperatures with increased stability.

The adducts of this invention can likewise be readily utilized to cure a wide variety of urethane resin compositions in various heat cured applications. These hardeners can be readily incorporated into urethane resin compositions by known mixing techniques familiar to practitioners skilled in the art.

The polyisocyanates which can be used in the curable polyurethane resin compositions include any of those commonly employed in making polyurethane plastics or resins such as toluene diisocyanate, 4,4-diphenylmethane diisocyanate, polyaryl polyisocyanates, and hexamethylene diisocyanate, or less conventional ones such as phenylindane diisocyanate. As is well known, resins made from such polyisocyanates are brittle so that for most purposes it is preferred to use the conventional polyisocyanate prepolymers having an average of more than a single isocyanate group per molecule, made by pre-reacting a molecular excess of a diisocyanate such as one of the foregoing with an organic material containing at least two hydroxyl groups per molecule and having a molecular weight of at least 300, such as castor oil, a hydroxy-terminated polyether, e.g., a polyalkylene glycol in which each alkylene group contains from 2 to 6 carbon atoms, a hydroxy-terminated polyester, particularly an aliphatic polyester of an alkylene glycol in which each alkylene contains 2 to 6 carbon atoms with an aliphatic polycarboxylic acid which contains in addition to the carboxyl group only hydrocarbon groups, the total number of carbon atoms in the acid being preferably from 3 to 10, or a hydroxy-terminated polybutadiene or butadieneacrylonitrile copolymer. Polyethers such as polyethylene glycol, polypropylene glycol and polytetramethylene glycol having molecular weights from 300 to 2,000 and polyesters such as the hydroxy-containing polyesters of any of the polyalkylene glycols, preferably those having 2 to 6 carbon atoms, with polycarboxylic acids containing from 3 to 10 carbon atoms and containing only hydrocarbon groups in addition to carboxyl groups are also preferred. Such polyesters have an average equivalent weight (based on hydroxyl groups) of 150–1,000 and have 2 to 4 hydroxyl groups per molecule. Prepolymers are preferred which are made by reacting at least two molecular proportions of a diisocyanate as described above with a polyalkylene glycol as described above to form a prepolymer having an equivalent weight (based upon isocyanate groups) of 400–1,500, but other prepolymers having an equivalent weight (isocyanate) within the same range are also desirable. Partially blocked polyisocyanates are also applicable.

When combined with polyurethanes at generally stoichiometric amounts and cured at elevated temperatures, the previously noted network of high crosslink density for epoxy resins is also evident with the urethanes. These systems can also be mixed with the various optional ingredients noted hereinabove as well as with typical urethane extenders and plasticizers.

The following examples will further illustrate the embodiments of the instant invention. In these examples, all parts are given by weight unless otherwise noted.

EXAMPLE 1

This example illustrates the preparation of a typical modified hardener of the instant invention.

An adduct of diethyl toluene diamine and diglycidyl ether of bisphenol A was made at a molar ratio of 4:1. 531 gm of diethyl toluene diamine (76% 2,4-diethyl isomer and 19% 4,6-diethyl isomer- ETHACURE 100 from Ethyl Corp.) were weighed into a reaction flask equipped with mechanical stirrer, thermometer and heating jacket. The flask was heated with stirring to 80°°C. 269 gm of preheated diglycidyl ether of bisphenol A (ARALDITE 6010 of CIBA-GEIGY Corp.) were added to the flask through a dropping funnel. The temperature was maintained at 80° C. for 2 hours with no exotherm. The temperature was raised to 100° C. and maintained for one hour with an exotherm to 125° C.

EXAMPLE 2

An adduct of diethyl toluene diamine and an epoxy phenol novolac resin was made at a molar ratio of 6:1. 680 gm of diethyl toluene diamine were weighed into a reaction flask equipped with a mechanical stirrer, thermometer and heating jacket. The flask was heated with stirring to 100° C. 120 gm of preheated epoxy phenol novolac resin (EPN 1138 from CIBA-GEIGY Corp.) were added slowly with stirring. After the addition was complete the temperature was maintained at 100° C. for 3 hours in order to complete the reaction.

EXAMPLES 3-4

The procedure of Example 1 was repeated utilizing the following components:

diglycidyl ether. The epoxy resin utilized for Formulations B-G hereinafter was an iron oxide filled epoxy blend utilizing 47 parts diglycidyl ether of bisphenol A and 3 parts 1,4-butanediol diglycidyl ether.

The following characteristics were then determined:

Mixed Viscosity—The viscosity of the blended epoxy-hardener system was measured with a Brookfield RVF viscometer using spindle #3 at 20 rpm at 23°-25° C. Samples were mixed for two minutes and the viscosity reading taken one minute thereafter.

Heat Deflection Temperature—Determined according to ASTM D-648-82. The liquid material was poured into a sheet mold, cured overnight at room temperature and then at the indicated cure schedule. The test was conducted using a load of 264 psi. on a sample size of 1.27 cm × 1.27 cm × 12.7 cm.

Pot Life—The specified quantities of mixed epoxy resin and hardener were reacted in a metal can at room temperature until cured. The time to complete cure was measured.

Thin Layer Tack Time—This test is a measure of the time needed to sufficiently cure a mixed system to a solid form such that a finger imprint remains visible on the surface. The test proceeds by depositing a 20 mil layer of the epoxy system on a surface, at room temperature, and periodically putting a finger imprint on the surface thereof.

|  | Parts | | | | | | |
| --- | --- | --- | --- | --- | --- | --- | --- |
|  | A | B | C | D | E | F | G |
| Example 1 adduct | 45 | — | — | — | — | — | — |
| Example 2 adduct | — | 35 | 28 | 85 | 90 | — | — |
| Example 3 adduct | — | 50 | 39 | — | — | 50 | 50 |
| Example 4 adduct | — | — | 9 | — | — | — | 35 |
| Triethylene tetramine | 50 | — | — | — | — | — | — |
| Diethyl toluene diamine | — | — | 9 | — | — | 35 | — |
| m-Xylene diamine | — | 15 | 15 | 15 | 10 | 15 | 15 |
| 1-Methyl imidazole | 5 | — | — | — | — | — | — |
| Ratio of modified epoxy resin to hardner | 100/13 | 100/17 | 100/16 | 100/13 | 100/15 | 100/16 | 100/17 |
| Mixed Visosity (cps) | 1660 | — | — | — | — | — | — |
| Heat Deflection Temp.* (°C.) | 141 | 146 | 146 | 148 | 152 | 145 | 143 |
| Cure Schedule | 1 | 2 | 2 | 2 | 2 | 2 | 2 |
| Pot Life (total wt. 175 gm) (min.) | 65 | — | — | — | — | — | — |
| Pot Life (total wt. 210 gm) (hrs.) | — | — | — | 35 | 50 | — | 20 |
| Thin Layer Tack Time (hrs.) | — | — | — | 16 | 20 | — | — |

*Cure Schedule

| 1 | 2 |
| --- | --- |
| 2 hrs/65° C. | 2 hrs./65° C. |
| 1 hr/95° C. | 2 hrs/95° C. |
| 1 hr/150° C. | 2 hrs/120° C. |
| 3 hr/170° C. | 2 hrs/150° C. |
|  | 4 hrs/170° C. |

|  | Parts | |
| --- | --- | --- |
|  | 3 | 4 |
| Diglycidyl ether of bisphenol A | 28.1 | — |
| 1,4-butanediol diglycidyl ether | — | 18.5 |
| Diethyl toluene diamine | 71.9 | 81.5 |

EXAMPLE 5

The following example is directed to the physical and performance characteristics of processed epoxy resins utilizing the hardeners of Examples 1-4.

The resin systems were prepared by blending the resin component with the optional ingredients and the hardener at room temperature. The epoxy resin utilized for Formulation A hereinafter was a blend of 65 parts diglycidyl ether of bisphenol A, 25 parts of epoxy phenol novolac (EPN 1138) and 10 parts of 1,4-butanediol These data thus illustrate the advantageous characteristics of epoxy resins containing the resinous hardener systems of the instant invention.

EXAMPLE 6

A cured polyurethane system was prepared by blending at room temperature 34 parts of the Example 1 adduct, 24 parts of dioctyl adipate plasticizer and 100 parts of a cycloaliphatic isocyanate urethane system (RP 6414 from REN Plastics). Upon curing at elevated temperatures, the solid urethane exhibited a 90-95 Shore A Hardness Value.

Summarizing, it is seen that this invention provides novel, modified hardener systems for epoxy and urethane resins which exhibit excellent performance characteristics. Variations may be made in proportions, procedures and materials without departing from the scope of the invention as defined by the following claims.

What is claimed is:

1. A hardener for epoxy resins comprising the adduct obtained from the reaction of diethyl toluene diamine and a polyepoxide having a functionality of at least two, said diamine being present in excess relative to said polyepoxide.

2. The hardener of claim 1, wherein said polyepoxide is selected from the group consisting of diglycidyl ether of bisphenol A, epoxy phenol novolacs, 1,4-butanediol diglycidyl ether, epoxy cresol novolacs, triglycidyl para-amino phenol, triglycidyl tris(p-hydroxyphenyl)methane, tetraglycidyl-1,1,2,2 tetrakis (p-hydroxyphenyl)ethane, vinyl cyclohexene dioxide, N,N,N$^1$,N$^1$-tetraglycidyl-4,4$^1$-methylene bis benzeneamine, N,N,N$^1$,N$^1$-tetraglycidyl meta-xylene diamine, diglycidyl aniline, resorcinol diglycidyl ether, catechol diglycidyl ether, hydroquinone diglycidyl ether, diglycidyl orthotoluidine, diglycidyl isophthalate, bisphenol F and S epoxy resins, and N,N,N$^1$,N$^1$-tetraglycidyl 1,3 bis-aminomethylcyclohexane.

3. The hardener of claim 1, wherein said polyepoxide corresponds to the formula

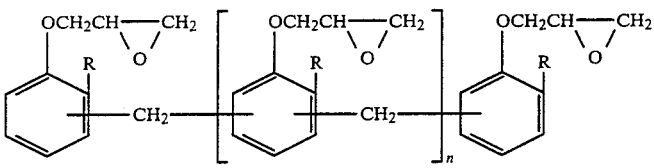

wherein R is hydrogen or methyl, and n is 0.2–3.4.

4. The hardener of claim 1, wherein said polyepoxide corresponds to the formula

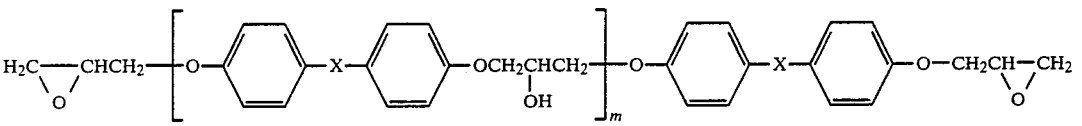

wherein m is 0–50 and X is —CH$_2$—,

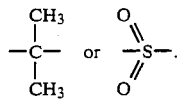

5. The hardener of claim 1, wherein said polyepoxide is 1,4-butanediol diglycidyl ether.

6. The hardener of claim 1, wherein from about 2 to 10 moles of diamine are present per mole of polyepoxide.

7. A curable mixture comprising (a) a polyepoxide compound and (b) a hardener according to claim 1.

8. The curable mixture of claim 7, wherein said polyepoxide compound is selected from the group consisting of epoxide resins based on polyhydric phenols, epoxidation products of cresol novolacs, epoxidation products of phenol novolacs, hydantoin epoxide resins, polyglycidyl esters, glycidylated aromatic amines, glycidylated aminophenols and cycloaliphatic epoxy resins.

9. The curable mixture of claim 7, wherein said hardener and said polyepoxide compound are present in stoichiometric amounts ±50%.

10. The curable mixture of claim 7 which also contains a maximum of 75%, by weight, of an aliphatic, cycloaliphatic or aromatic primary or secondary amine.

11. The curable mixture of claim 10, wherein said amine is selected from the group consisting of monoethanolamine, N-aminoethyl ethanolamine, ethylenediamine, hexamethylenediamine, trimethylhexamethylenediamine, diethylenetriamine, triethylenetetramine, tetraethylenepentamine, N,N-dimethylpropylenediamine-1,3, N,N-diethylpropylenediamine-1,3, bis(4-amino-3-methylcyclohexly)methane, bis(p-aminocyclohexyl)methane, 2,2-bis(4-aminocyclohexyl)propane, 3,5,5-trimethyl-s-(aminomethyl)-cyclohexylamine, N-aminoethyl-piperazine, m-phenylene-diamine, p-phenylenediamine, bis(p-aminophenyl)methane, bis(p-aminophenyl)-sulfone, m-xylylenediamine, 1,2-diaminocyclohexane, 1,4-diaminocyclohexane, toluene diamine, 1,3-bis(aminomethyl)cyclohexane, 1-4-bis-(aminomethyl)cyclohexane, isophorone diamine and 1-methyl-imidazole.

12. The curable mixture of claim 7, wherein in said hardener said polyepoxide corresponds to the formula

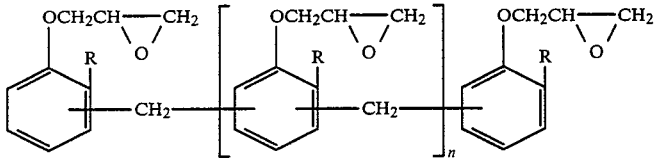

wherein R is hydrogen or methyl, and n is 0.2–3.4.

13. The curable mixture of claim 7, wherein in said hardener said polyepoxide corresponds to the formula

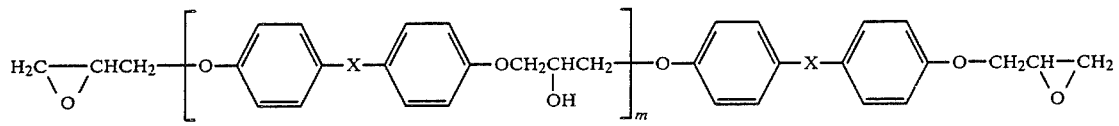

wherein m is 0-50 and X is —CH₂—,

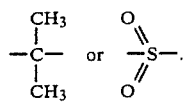

14. The curable mixture of claim 7, wherein 1,4-butanediol diglycidyl ether is the polyepoxide in said hardener.

15. The curable mixture of claim 7, wherein in said hardener from about 2 to 10 moles of diamine are present per mole of polyepoxide.

16. The product obtained by curing the mixture of claim 7 at elevated temperatures.

17. The product obtained by curing the mixture of claim 10 at elevated temperatures.

18. A curable mixture comprising (a) a urethane resin and (b) a hardener according to claim 1.

19. The product obtained by curing the mixture of claim 18 at elevated temperatures.

* * * * *